United States Patent [19]

Clarke

[11] Patent Number: 4,856,755
[45] Date of Patent: Aug. 15, 1989

[54] FLOW CONTROL

[76] Inventor: Ellis W. Clarke, 47 Deramore Avenue, Belfast, Northern Ireland, BT9 5JS

[21] Appl. No.: 276,600

[22] Filed: Nov. 28, 1988

[30] Foreign Application Priority Data

Nov. 26, 1987 [GB] United Kingdom ............... 8727683

[51] Int. Cl.$^4$ ............................................. F16K 7/04
[52] U.S. Cl. ........................................ 251/6; 251/4; 604/250
[58] Field of Search ................. 251/4, 6; 604/34, 250

[56] References Cited

U.S. PATENT DOCUMENTS

| 3,893,468 | 7/1975 | McPhee ............................... 251/6 X |
| 4,066,238 | 1/1978 | Clarke .................................... 251/6 |
| 4,475,708 | 10/1984 | Beeher, Jr. .............................. 251/6 |

Primary Examiner—John Fox
Attorney, Agent, or Firm—Scrivener and Clarke

[57] ABSTRACT

A device for controlling the flow of a parenteral fluid, comprises a resilient tubular body of an infusion tube having a flattened portion with two parallel opposed walls. Each wall has a tapering groove, the grooves together defining a longitudinal region of non-contact between the walls of tapering cross-section. Regulating means is provided for flexing a short length of the body about a longitudinal axis of the body so as to urge the two walls together so that the rate of flow is determined by the cross-section of the region of non-contact at said length. Flexure about the longitudinal axis of the body avoids cold-flow of the region of non-contact. The regulating means comprises a support and an operating member longitudinally movable relative to the support, the body being flexed at said length by the co-operation of the support and the operating member. The support is preferably a channel having side walls which define grooves to guide a roller for longitudinal movement relative to the channel. Either the support or the roller has a rib, while the other has a complementary groove. A central part of the body is flexed into the groove by the rib.

7 Claims, 1 Drawing Sheet

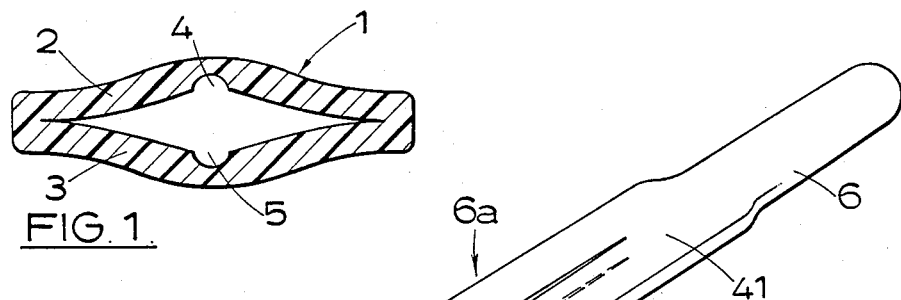
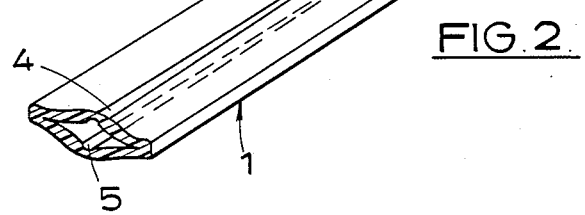
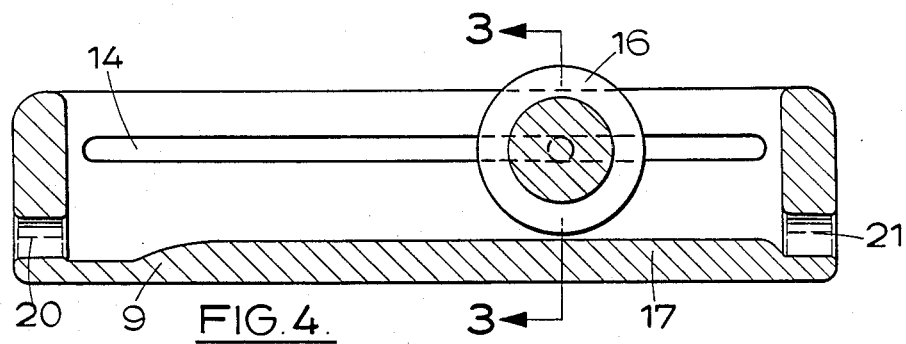
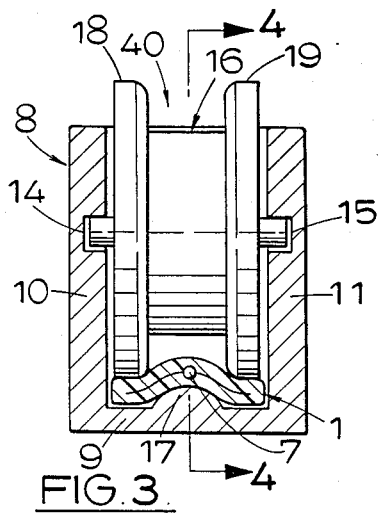
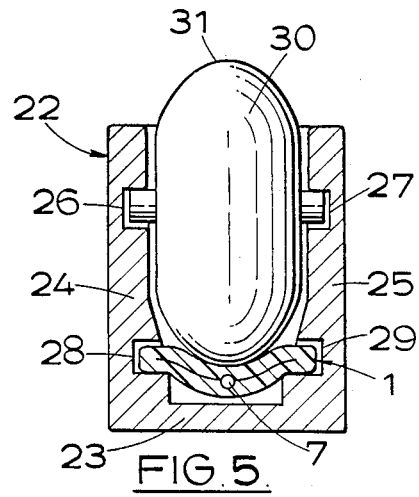

FLOW CONTROL

The present invention relates to devices for controlling flow of fluid. The invention is primarily concerned with the control of the flow of liquids, but the invention may also apply to control of the flow of gases.

In the administration of liquids such as blood, saline or other parenteral solutions to a patient undergoing medical treatment it is conventional for a container, containing a supply of the liquid, to be suspended above the level of the patient and for the liquid to flow to the patient through an infusion tube provided with control means to control the rate of flow of liquid through that tube. The control means is usually adjustable so that the rate of flow of liquid can be adjusted. The normal range of flow rates is from 1 ml to 400 ml per hour. Conventional flow-control means are operable to achieve these flow rates, and may indeed also have a setting in which relatively unrestricted flow is permitted.

Many methods for controlling the flow of parenteral solutions have been suggested. One method which has been widely used employs a device known as a roller clamp. Roller clamps have been described in, for example, the specifications of U.S. Pat. Nos. 3,099,429, 3,685,787, 3,802,463, 3,900,184, 3,960,149, 4,013,263, 4,047,694, 4,065,093, and 4,340,201, British Patents Nos. 1,319,090, 1,400,995, 1,561,094 and 2,018,398, and International Patent Application Nos. WO81/01600 and WO85/02240.

Conventionally the body of a roller clamp is shaped like a channel with open ends and consists of a rectangular base with two upstanding side walls. A cylindrical roller is retained within the body by trunnions which fit loosely into longitudinal grooves in the side walls and it can be rolled along the base using the thumb. An infusion tube is placed between the roller and the base where it becomes compressed by the roller in a manner which differs according to whether the clamp is of the 'original' or 'improved' type.

In the 'original' type the grooves in the side walls are inclined relative to the base so that the roller presses the infusion tube against the base in a progressively increasing manner as it is rolled along the channel. When the tube is compressed in this way the interior of the tube becomes largely closed owing to the engagement of the flattened walls of the tube, and the flow of liquid is confined to two small side passageways remaining at the edges of the flattened section. These edges are under considerable stress and at any given roller setting become slowly flattened by a process of 'cold-flow' or 'creep' of the plastics material of the infusion tube. As these edges creep, the side passageways within them become smaller in cross-section and the flow of liquid is gradually reduced; in many cases it will eventually stop altogether.

The 'improved' type of roller clamp has been designed to reduce this cold-flow effect. The clamp is of a similar general form to the 'original' clamp except that it has a longitudinal tapered groove of V-shaped cross-section formed in its base, and the grooves in the side walls are parallel with the base and are located at a distance from the base such as to cause the infusion tube to be compressed tightly enough to close the side passageways in the tube. When the tube is compressd in this way part of the wall of the flattened tube overlying the tapered groove in the base becomes displaced into the groove and so leads to the formation of a central passageway in the tube to provide for the flow of liquid.

The stresses in the material of the tube displaced into the central channel of the 'improved' clamp are less than those at the edges in the 'original' type so that constancy of flow is not as severely affected by cold-flow of the plastics material. However, cold-flow of the plastics material is not entirely avoided. The cross-sectional area of the central passageway in the tube is determined principally by the width of that part of the tapered groove under the roller at any particular setting, and also the thickness and physical properties of the walls of the tube. The cross-sectional area of the passageway in the infusion tube is reduced in size progressively as the roller is moved nearer to the narrower end of the tapered groove and the passageway usually becomes completely closed before the roller reaches the end of the groove.

In both types of clamp portions of the channels at the high-flow end of the body are usually displaced considerably from the base member to provide a roller setting for unrestricted flow. In some cases this also facilitates the insertion of the tube into the clamp during manufacture.

Tests have shown that the effects of the cold-flow of the material of the infusion tube cause the flow-rate to fall exponentially with time from any value that is originally set. Hence the nursing staff have to check and readjust both 'original' and 'improved' roller clamps repeatedly and at relatively frequent intervals. When a clamp has been adjusted to a new setting the infusion tube may take time to recover from any deformation; as a consequence the flow rate again tends to alter with time. The problems of setting these roller clamps are further increased by the relatively large changes in flow produced by relatively small movements of the roller. In both these types of clamp the full working range of flow is usually no more about 5 millimetres of movement of the roller.

In an attempt to overcome the problems of cold-flow creep of the compressed tube and restricted passageway of the infusion tube it has been proposed in British Patent No. 1 361 405 (equivalent to U.S. Pat. No. 3,779,507) to incorporate a tapering formation inside a tubular body of the infusion tube. The tapering formation may comprise one or more tapered grooves or a tapered wire. Opposed walls of a length of the tube are formed into a flattened region in which they can lie against each other. In use the walls of the tube can part to allow relatively unrestricted flow. At a selected location, the walls of a short length of the tube are caused to come together so that the rate of flow is determined by the cross-sectional area of the tapering formation at that location. GB 1 361 405 discloses the use of a clamp to hold the walls of the tube together locally. This works well but requires the use of two hands to effect adjustment of the clamp. It also relies on resilient means to urge the jaws of the clamp together, something that may lead to occasional failure.

In the last paragraph of the specification of GB 1 361 405 is a description of a modified clamp which superficially resembles a roller clamp: one jaw is constituted by the flat base of a channel and the other jaw is constituted by a roller. The spacing of the roller from the flat base remains uniform throughout the travel of the roller. That spacing is critical and must remain absolutely constant at each position of adjustment. That modified clamp suffers from the practical disadvantage that its successful operation depends on very fine tolerances in manufacture; throughout the length of adjustment of the roller the thickness of the flattened tube, with its opposed walls lightly touching each other, must be uniform and of a predetermined value, while the gap between the roller and the flat base must likewise be uniform and of a predetermined value throughout the length of adjustment of the roller. If there is any variation in these dimensions the precise control of the flow becomes impossible. Moreover, the roller is maintained in any position of adjustment by a force applied to it by the flattened tube, which must therefore be lightly compressed beneath the roller. Any minor variations in the thickness of the tube or of the spacing between the roller and the base will therefore cause considerable variation in the force applied to the roller and thus to the resistance to adjustment of the roller. Such requirements of fine tolerances cannot readily be met in normal manufacture.

An improvement to the proposal of GB 1 361 405 is suggested in British Patent No. 1 539 371 (equivalent to U.S. Pat. No. 4,066,238) in which a flattened tube, with its internal tapering formation, is locally kinked in order to cause the side walls of the tube to remain in contact with each other in spite of the pressure of fluid in the tube. Various devices for kinking the tube are described and illustrated in GB 1 539 371. Two of the devices illustrated incorporate thumb-wheels; one is shown in FIGS 26 and 27 and the other is shown in FIGS. 28 and 29. In each instance, however, the roller is mounted for rotation about an axis that is fixed in relation to a body, and in use, when adjustment is carried out the whole body moves lengthwise relative to the tube. Consequently, adjustment requires a form of manipulation different form that in common use with known roller clamps. This unfamiliar form of manipulation introduces its own problems when the device is used in practice.

Another problem with the device shown in GB 1 539 371 arises from the fact that the presence of the kink necessarily requires a change in direction of the tube. In the first of the two versions illustrated (FIGS. 26 and 27), end portions of the tube are shown at an angle approaching 90°, something that would normally be inconvenient in use. In the other of the versions illustrated (FIGS. 28 and 29) guides are provided to bring the end portions into alignment, but this requires bending the tube without kinking it, something that is difficult to achieve unless the device is relatively long.

The embodiment of FIGS. 28 and 29 uses a series of teeth on the roller to engage teeth on the flattened region of the tubular body and suffers in addition from some backlash because of the soft nature of the teeth moulded into the plasticised PVC material of the tubular body.

These various factors combine to reduce the precision with which adjustments can be made and increase the time spent in regulating the flow. These versions of the device also impose problems in the manufacture of the tubular body, such as the forming of the teeth and the provision of end-stops, and there are other provlems associated with the moulding and assembly of the bending means.

It is the aim of the present invention to alleviate at least some of the problems discussed above.

According to the invention a device for controlling fluid flow comprises a tubular body, defining a passageway, having opposed flexible and resilient walls which for at least a portion of the axial length of the tubular body are capable of being held in mutual contact throughout their cross-section except for a limited non-contacting region, this region being of a cross-section which varies along the general direction of flow through the passageway, and regulating means comprising a longitudinally extensive support by means of which said portion of the tubualar body is supported, and an operating element which is movable lengthwise of the support, the support and the operating element co-operating to cause flexure of a relatively short length of said portion of the tubular body immediately adjacent to the operating element, about a substantially longitudinal axis, the walls of said length of the tubular body not being clamped together but being prevented from separating, when subjected to the pressure of fluid in the tube, owing to the cross-sectional shape of said length resulting from said flexure, the walls of the remainder of said portion of the body being parted in use (unless restrained by other means) so that the rate of flow of fluid through said portion of the tubular body is determined by the cross-section of the non-contacting region of the walls at said length.

The invention is based on the concept of using an operating element to flex the tubular body locally about a longitudinal axis. Since it is the flexing of the body, not the clamping of the tube, that prevents the body from opening, the tolerances required in manufacture are far less critical than those required in the manufacture of a device of the kind described in GB 1 361 405 and discussed above. If the operating element flexes the body either a little more or a little less than the designed degree of flexing, the operation of the device is not significantly affected.

A further advantage of the present invention is that as the tubular body is resilient is will exert a force on the operating element serving to retain the element in any selected position of adjustment.

In one design the support has a longitudinal rib for engagement with an intermediate part of said portion of the tubular body, between marginal parts thereof, and the operating element has spaced bearing means for engagement with marginal parts of said portion. Preferably the rib terminates short of the end of said portion so that when the operating element is moved to a position of adjustment beyond the rib, it no longer causes the opposed walls of the body to be held in mutual contact.

In another design the support has a longitudinal groove for receiving an intermediate part of said portion of the tubular body, between marginal parts thereof, and the operating element has bearing means for engagement with said intermediate part so as to cause it to enter said groove. Preferably the operating element can be moved to a position of adjustment in which it no longer causes the opposed walls of the body to be held in mutual contact.

The support preferably constitutes the base of a channel having walls with guide formations for guiding the operating element.

The operating element preferably comprises a roller, although it could, if desired, comprise a non-rotatable slider.

A device incorporating a roller has a significant advantage in that it may be arranged to be operated by the user in a manner very similar to, if not identical with, that in whch the well-known, conventional roller clamps are used. It can thus be introduced into general use with the minimum of special instruction to the medical staff.

The position of the operating element relative to the support provides a clear indication of the resistance to flow being offered by the device and can be of help during clinical use. Should a partial obstruction occur somewhere in the infusion system it will cause a reduction in the rate of flow of liquid to the patient. An operator will normally compensate for this reduction by moving the operating element to a more 'open' position and a series of such adjustments may be made over several hours. The resulting lack of correspondence between the observed rate of flow and the abnormal position of the operating element will then warn a skilled user of the presence of the obstruction and that he or she should carefully examine the infusion system and the patient's veins. This feature is enhanced by giving the operating element a colour which contrasts sharply with that of the regulator body.

It will be appreciated that as far as the tubular body is concerned, the non-contacting region in which the walls are not in mutual contact may be formed by a tapering groove in one of the walls, or preferably by mutually aligned tapering grooves in both walls so that a tapering passage of circular or substantially circular cross-section is formed when the walls are held in mutual contact. When the walls of the tubular body are held in mutual contact over only a portion of their axial length, as by means of the flexion caused by the operating element, the tapering passage so formed in this localised area provides the only flow path for the fluid. Upstream and downstream of this area the resilient nature of the walls causes them to move apart so that the resistance to flow through these other parts of the body is relatively low. By moving the operating element, and thus the localised area of contact of the walls along the passageway, the parts of the tapering grooves which form the tapering passage can be altered so that the rate of flow of a fluid through the body is altered.

The tapering grooves may be arranged to end at a suitable distance from the end of the tubular body, so that when the operating element is adjacent to the ungrooved part of the body, flow is prevented.

The tube from which the tubular body is made preferably comprises a flexible and resilient thermoplastic synthetic resin, such as polyvinyl chloride. The profile of the body may be made by permanently deforming a tube that is originally of circular cross-section about a suitably shaped solid former using heat. A method of forming the body is described in the specification of British Patent No. 1 361 405 at page 2 lines 63 to 122, which are incorporated herein by cross-reference.

The shape of the solid former determines the flow characteristics of the device and it can be selected so as to be appropriate to the needs of the administration set, whether for example for general or paediatric use or for more viscous fluids such as blood. Furthermore, the shape of the former can also be arranged to produce a tapering non-contacting region that maximises the fineness of flow control by enabling the whole travel of the operating element to correspond with the working range of flows required. If necessary the tapering passage can be arranged to give a disproportionately greater travel, and thus a finer control, at the slower rates of flow. The amount of travel provided to encompass the working range of flow is typically 50 millimetres.

In one preferred embodiment of device in accordance with the invention the support comprises a base which has a longitudinal rib at or near its centre. The cross-sectional profile of the rib can be any convenient shape but a semicircular shape is preferred. The operating element preferably comprises a roller having a peripheral groove which in section is larger than, and arches over, the rib. The groove has such a depth that when the tubular body is placed between the roller and the base it is locally flexed over the raised area without the roller compressing that part which lies along the top of the rib and which contains the tapering passage. The sides of the roller forming the walls of the groove, constitute bearing means that bear against marginal parts of the tubular body and cause the flexible walls of the tubular body to contact each other over a localised area so that the tapering passage at that point defines the flow rate.

In anothr preferred embodiment of the device the sides of the tubular body are located in appropriately-sized grooves in the side walls of a channel, and a roller has a peripheral rib which causes the tubular body to be flexed locally about a longitudinal axis in the opposite direction from that in which flexing occurs in the first embodiment. The flexure however has the same effect of causing the flexible walls of the tubular body to contact each other over a localised area, and causing the tapering passage to remain uncompressed by the roller and thus vertually unaffected by cold-flow in the material of the wall.

The end of the regulating means adjacent to the wide end of the tapering passage may be provided with a free-flow position for the roller either by inclining guide means for the roller away from the base or, in the case of the first preferred embodiment of the device, discontinuing the rib, or even replacing a portion of it with a hollowed out area. Preferably means is also provided for holding the end tubes leading to and from the tubular body as they extend through longitudinally spaced ends of the channel in order to prevent any accidental longitudinal displacement of the tubular body relative to the support during use.

The channel may be moulded in a flat form, and the side walls then folded up for assembly around the tubular body and operating element, the ends being riveted or welded near to where they engage the end-tubes. The edges of the roller may be knurled to provide increased friction with the ball of the thumb.

Two preferred embodiments of the present invention will now be described in greater detail, by way of example only, with reference to the accompanying drawings, in which:

FIG. 1 is a local cross-section through a tubular body with flexible walls, passageway and tapering grooves that form a tapering passage, FIG. 2 is a perspective view of part of the tubular body shown in FIG. 1, and illustrates the manner in which the tapering grooves taper, FIG. 3 is a cross-section through a first form of device embodying the present invention, the section being along the line 3—3 of FIG. 4, FIG. 4 is a longitudinal cross-section to a smaller scale, along the line 4—4 of FIG. 3, and shows the first form of the clamp when it is in use, and FIG. 5 is a cross-section through a second form of devie embodying the present invention.

FIGS. 1 and 2 show details of a tubular body 1 of a known kind for use in controlling the flow of parenteral liquid to a patient. The body has a flattened portion 6a interposed between two cylindrical unflattened end tubes 6. The flattened portion 6a is defined by opposed flexible walls 2 and 3 each of which is formed with a tapering groove 4,5 in its inner face. Each of the grooves 4,5 extends longitudinally along a central part of the body and the grooves are mutually aligned so that when the walls 2,3 are brought together in mutual contact the tapering grooves 4,5 together define a tapering passage 7 along the centre of the body. In an unstressed state the walls 2 and 3 take the form shown in FIG. 1.

The body 1 is formed by deformation using heat and pressure of a tube of thermoplastic polymer. Details of a method of manufacture of the tubular body 1 are given in the specification of the aforementioned British Patent No. 1 351 405.

The tubular body 1 is used in combination with a regulator adapted to flex a relatively short length of the flattened portion 6a about a longitudinal axis of the flattened portion. One form of regulator is shown in FIGS. 4 and 5 and comprises a channel 8 consisting of a base 9 and two side walls 10 and 11. The side walls 10 and 11 are formed with opposed and aligned parallel grooves 14 and 15. A roller 16, constituting an operating element, has trunnions that enter the grooves 14 and 15 so that it can be moved longitudinally along the channel 8. The roller 16 has opposed flanges 18 and 19 which constitute spaced bearing means and which define a peripheral groove 40 between them. The base of the regulator has a raised rib 17 which registers with the circumferential depression of the roller.

The grooves 14 and 15 extend longitudinally, parallel to the base 9, so that when the roller 16 is moved longitudinally it maintains a substantially constant distance from the base 9. The rib 17 extends longitudinally of the base and terminates short of one end of the regulator. Circular apertures 20 and 21 are provided at opposite ends of the regulator to grip lightly the end tubes 6 of the tubular body and so prevent its accidental displacement lengthwise of the channel.

In use, the body 1 is mounted in the channel with its end tubes 6 extending through the apertures 20, 21 and being lightly gripped by them. The flattened portion 6a is located between the base 9 and the roller 16 with the narrower portions of the tapering passage 7 towards the right end of the channel as seen in FIG. 4. The passage 7 tapers to nothing before the end of the raised rib 17 so as to leave a short length 41 of the flattened portion with no passage 7. The short length 41 overlies the rib 17 adjacent aperture 21. It may be desirable to locate the roller 16 adjacent the lefthand end of the channel, above the region of the base that has no rib 17, when introducing the body into the channel.

FIG. 3 shows the principle of operation of the device. The user holds the regulator, fitted with the body, in the palm of one hand and operates the roller with the thumb of that hand. The other hand is free for other operations. When the roller 16 is moved to a position of adjustment over an intermediate part of the rib 17 the flanges 18 and 19 bear locally on marginal parts of the flattened portion of the body and thus urges those parts of the body towards the base 9. This pushes a central region of the body against the rib 17, that central region entering the peripheral groove 40. In the immediate neighbourhood of the roller a short length of the flattened portion 6a is flexed about a longitudinal axis. It will be noted that this length of the body is not clamped but is merely caused to flex. The flexing of the body urges the walls 2 and 3 together. It will also be noted that the marginal parts of the body do not touch the base 9. Flexing of the body results in the walls being held in mutual contact except for a limited non-contacting region defined by the tapering passage. The cross-sectional area of that passage depends on the position of the roller, and it determines the rate of flow of liquid through the body. By moving the roller longitudinally of the body the flattened portion can be flexed at different longitudinally spaced locations to give different flow-rates.

When the roller 16 is over portion 41 of the body, where there is no passage 7, flow of liquid through the body is prevented. When the roller 16 is adjacent to the aperture 20 and does not overlie the rib 17, the body is not flexed, the walls 2 and 3 are not urged together, and a relatively free flow of fluid through the body is possible.

An operator can use the regulator in the same way as an existing roller clamp, but the present invention overcomes the serious problem of plastic creep. Since the degree of flexing of the body is not critical to the control of flow, the regulator can be manufactured to normal tolerances.

FIG. 5 is a cross-section through a second form of the regulator with the same tubular body 1 in its position of use. The regulator comprises a channel 22 consisting of a base 23 and two side walls 24 and 25 formed with two pairs of opposed grooves 26,27 and 28,29 which extend parallel to one another and to the base for the majority of the longitudinal length of the channel. A roller 30 has trunnions which enter the grooves 26 and 27 so that it can be moved longitudinally along the channel. The roller 30 has a peripheral rib 31. The body 1 lies beneath the roller 30 and above the base 23, and marginal parts thereof are located in the grooves 28 and 29.

In use the peripheral rib 31 on the roller 30 causes a relatively short length of the tubular body 1 to flex about a longitudinal axis of the tube and so causes the flexible walls of the tubular body to contact each other over a localised area but to leave the tapering passage 7 open.

Towards that end of the channel corresponding to the location in which the rib 9 was foreshortened in the first form of device illustrated, the grooves 26 and 27 are inclined upwards, away from the base 23. In use, when the roller 30 is adjusted to a position such that its trunnions move up the inclined parts of the grooves, the rib 31 moves out of contact with the body 1 and thus permits relatively free flow to occur through the body.

What is claimed:

1. A device for controlling fluid flow comprising a tubular body defining a passageway having opposed flexible and resilient walls which for at least a portion of the axial length of the tubular body are capable of being held in mutual contact throughout their cross-section except for a limited non-contacting region, this region being of a cross-section which varies along the general direction of flow through the passageway, and regulating means comprising a longitudinally extensive support by means of which said portion of the tubular body is supported, and an operating element which is movable lengthwise of the support, the support and the operating element co-operating to cause flexure of a relatively short length of said portion of the tubular body immediately adjacent to the operating element, about a substantially longitudinal axis, the walls of said length of the tubular body not being clamped together but being prevented from separating, when subjected to the pressure of fluid in the tube, owing to the cross-sectional shape of said length resulting from said flexure, the walls of the remainder of said portion of the body being parted in use, unless restrained by other means, so that the rate of flow of fluid through said portion of the tubular body is determined by the cross-section of the non-contacting region of the walls at said length.

2. A device according to claim 1 in which the support has a longitudinal rib for engagement with an intermediate part of said portion of the tubular body, between marginal parts thereof, and the operating element has spaced bearing means for engagement with marginal parts of said portion.

3. A device according to claim 2 in which the rib terminates short of the end of said portion so that when the operating element is moved to a position of adjustment beyond the rib, it no longer causes the opposed walls of the body to be held in mutual contact.

4. A device according to claim 1 in which the support has a longitudinal groove for receiving an intermediate part of said portion of the tubular body, between marginal parts thereof, and the operating element has bearing means for engagement with said intermediate part so as to cause it to enter said groove.

5. A device according to claim 4 in which the operating element can be moved to a position of adjustment in which it no longer causes the opposed walls of the body to be held in mutual contact.

6. A device according to claim 1 in which the support constitutes the base of a channel having walls with guide formations for guiding the operating element.

7. A device according to claim 1 in which the operating element comprises a roller.

* * * * *